US00RE42152E

(19) United States
(12) Reissued Patent
Bridger et al.

(10) Patent Number: US RE42,152 E
(45) Date of Reissued Patent: Feb. 15, 2011

(54) AROMATIC-LINKED POLYAMINE MACROCYCLIC COMPOUNDS WITH ANTI-HIV ACTIVITY

(75) Inventors: Gary J. Bridger, Bellingham, WA (US); Sreenivasan Padmanbhan, Exton, PA (US); Renato Skerlj, Newton, MA (US); David M. Thornton, Reading (GB)

(73) Assignee: Genzyme Corporation, Cambridge, MA (US)

(21) Appl. No.: 12/192,704

(22) PCT Filed: Dec. 16, 1992

(86) PCT No.: PCT/GB92/02334

§ 371 (c)(1),
(2), (4) Date: Aug. 18, 1994

(87) PCT Pub. No.: WO93/12096

PCT Pub. Date: Jun. 24, 1993

Related U.S. Patent Documents

Reissue of:
(64) Patent No.: 5,583,131
Issued: Dec. 10, 1996
Appl. No.: 08/244,863
Filed: Aug. 18, 1994

(51) Int. Cl.
*C07D 401/14* (2006.01)
*C07D 403/10* (2006.01)
*A61K 31/395* (2006.01)
*A61K 31/555* (2006.01)

(52) U.S. Cl. ..... 514/183; 514/184; 540/474; 540/465

(58) Field of Classification Search ..... 514/183, 514/184; 540/465, 474
See application file for complete search history.

(56) References Cited

U.S. PATENT DOCUMENTS

| | | | | |
|---|---|---|---|---|
| 5,021,409 | A | | 6/1991 | Murrer et al. |
| 5,047,527 | A | | 9/1991 | Handel et al. ..... 540/479 |
| 5,047,572 | A | * | 9/1991 | Michaely et al. ..... 560/11 |
| 5,374,416 | A | | 12/1994 | Rousseaux et al. |

FOREIGN PATENT DOCUMENTS

| | | | |
|---|---|---|---|
| EP | 0 296 522 | A2 | 12/1988 |
| EP | 0 434 385 | A2 | 6/1991 |
| EP | 0 305 320 | B1 | 9/1992 |
| GB | 91/26677 | | 12/1991 |
| WO | WO 91/05762 | A1 | 5/1991 |
| WO | WO 92/16494 | A1 | 10/1992 |
| WO | 92/16494 | | 10/1992 |
| WO | WO 93/12096 | | 6/1993 |

OTHER PUBLICATIONS

Diril, et al.; "Simulation strategies for unusual EPR spectra of binuclear mixed–valence manganese complexes: synthesis, properties, and x–ray structures of the MnIIMnIII complexes [Mn2(bpmp)(.mu.–OAc2](CIO4)2.cntdot.H2O and [Mn2(bcmp)(.mu.–OAc2](CIO4)2.cntdot.CH2CI2"; Journal of the American Chemical Society; 1989; 111 (14):5102–5114.*

De Clercq et al.; Potent and selective inhibition of human immunodeficiency virus (HIV)–1 and HIV–2 replication by a class of bicyclams interacting with a viral uncoating event; Jun. 1992; Proc. Natl. Acad. Sci. USA; 89: 5286–5290.*

Alcock et al., "Studies of Pendant–arm Macrocyclic Ligands. Part 4. Two Penta–aza Macrocycles based on 1–(2'–Dimenthylaminoethyl)–1,5,9,13–tetra–azacyclohexadecane and its Complexes with Bivalent Metal Ions," *J. Chem. Soc. Dalton Trans.*, pp. 1361–1364 (1985).

Baba et al., "Sulfated Polysaccharides as Potent Inhibitors of HIV–Induced Syncytium formation: A New Strategy Towards AIDS Chemotherapy," *J. AIDS* 3:493–499 (1990).

Barefield et al., "Characterization of 2,2'–Bi–(1,4,8,11–tetra–azacyclotetradecane): X–Ray Structure and Properties of the Dinuclear Complex [Ni2(C20H46N8)][CIO4]4," *J.C.S. Chem. Comm.*, pp. 302–304 (1981).

Bridger et al., "Synthesis and Structure–Activity Relationships of Phenylenebis(methylene)–Linked Bis–Tetraazamacrocycles That Inhibit HIV Replication. Effects of Macrocyclic Ring Size and Substituents on the Aromatic Linker," *J. Med. Chem.* 38:366–378 (1995).

Chandler et al., "Synthesis of some 2,9–Disubstituted–1, 10–phenanthrolines," *J. Heterocycl. Chem.* 18(3):599–601 (1981).

De Clercq, "The Bicyclam AMD3100 Story," *Nature Reviews* 2:581–587 (2003).

Diril, "Synthesis and Characterization of Binucleating Ligands and Their Manganese Complexes as Models for the Oxidation of Water to Molecular Oxygen," Dissertation, Rutgers, The State University of New Jersey (1988).

Dischino et al., "Synthesis of Nonionic Gadolinium Chelates Useful as Contrast Agents for Magnetic Resonance Imaging. 1,4,7–Tris(carboxymethyl) –10–substituted–1,4,7, 10–tetraazacyclododecanes and Their Corresponding Gadolinium Chelates," *Inorg. Chem.* 30:1265–1269 (1991).

Fabbrizzi et al., "Ditopic Receptors for Transition–Metal Ions: A Heterobimetallic Nickel(II)–Copper(II) Bis(macrocyclic) Complex and Its Stepwise Oxidation to the Tervalent State," *Inorg. Chem.* 25:2671–2672 (1986).

Griffing et al., "2,5–bis–(Chloromethyl)–thiophene and Some of its Derivatives," *J. Am. Chem. Soc.* 70:3416–3419 (1948).

Haeg et al., "Anthraquinone–Based Cyclophane Hosts: Synthesis and Complexation Studies," *J. Am. Chem. Soc.* 111(2):692–696 (1989).

(Continued)

*Primary Examiner*—Ardin Marschel
*Assistant Examiner*—Savitha Rao
(74) *Attorney, Agent, or Firm*—Finnegan, Henderson, Farabow, Garrett & Dunner, LLP

(57) ABSTRACT

Polyamine macrocyclic compounds, e.g. of 10 to 15 ring members and 3 to 6 ring amine nitrogens, linked through methylene groups to an aromatic moiety, show high selective activity against HIV.

43 Claims, No Drawings

OTHER PUBLICATIONS

Joao et al., "Quantitative Structural Activity Relationship Study of Bis–Tetraazacyclic Compounds. A Novel Series of HIV–1 and HIV–2 Inhibitors," *J. Med. Chem.* 38:3865–3873 (1995).

Mirriam–Webster's Collegiate Dictionary, 10$^{th}$ Edition p. 794 (2000).

Momenteau et al., "Both–faxes Hindered Porphyrins. Part 2. Synthesis and Characterization of internally Five–co–ordinated Iron (II) Basket–handle Porphyrins derived from 5,10, 15,20–Tetrakis (o–hydroxyphenyl)porphyrin," *J. Chem. Soc. Perkin Trans.,* pp. 61–70 (1985).

Pauwels et al., "Rapid and automated tetrazolium–based colorimetric assay for the detection of anti–HIV compounds," *J. Virol. Methods* 20:309–321 (1988).

Schneider et al., "Synthesis of Two Bis–tetraaza–macrocycles and Study of the Structures, Electrochemistry, VIS and EPR Spectra of their Binuclear Cu2+ and Ni2+ complexes," *Helv. Chim. Acta.* 68:53–61 (1985).

U.S. Appl. No. 08/244,863, filed Aug. 18, 1994.

Wieghardt et al., "A Novel Mixed–valent MnIII–MnIV–Dimer,[L2Mn2(μ–O)2(μ–MeCO2)][BPh4]2 MeCN: Crystal Structure, Magnetic Properties, and E.S.R. Spectrum (L=1,4,7–triazacyclononane)," *J. Chem. Soc. Chem. Commun.,* pp. 651–653 (1987).

Wieghardt et al., "Zweikernige Mangan(II,III,IV)–Modellkomplexe fuer das active Zentrum des Metalloproteins Photosystem II: Darstellung, Magnetismus und Kristallstruktur von [LMnIII(μ–CH3CO2)2MnIVL][ClO4]3(L=N, N',N"–Trimethyl–1,4,7–triazacyclononan)," *Angew. Chem.* 98:1026–1027 (1986).

Ciampolini, M. et al. "Dinickel and Dicopper Complexes with N,N–Linked Bis(cyclam) Ligands. An Ideal system for the Investigation of Electrostatic Effects on the Redox Behavior of Pairs of Metal Ions" *Inorganic Chem.* 26(21):3527–3533 (1987).

Schneider, R. et al. "Metal Complexes with Macrocyclic Ligands" *Helvitica Chimica Acta* 69(1):53–61 (1986).

Yaouanc, J–J. et al. "Mono N–Functionalization of Cyclic and Linear Tetraamines via Their Tridentate Tricarbonylchromium Complexes" *J. Chem. Soc. Chem. Commun.* 206–207 (1991).

* cited by examiner

AROMATIC-LINKED POLYAMINE MACROCYCLIC COMPOUNDS WITH ANTI-HIV ACTIVITY

Matter enclosed in heavy brackets [ ] appears in the original patent but forms no part of this reissue specification; matter printed in italics indicates the additions made by reissue.

This application is the [356USC371 Nation] *35 U.S.C. 371 National* Stage of PCT/GB92/02334, filed Dec. 16, 1992, *which claims the benefit of priority to GB 91/26677, filed Dec. 16, 1991.*

This invention concerns improvements in chemical compounds, more especially it concerns compounds and pharmaceutical compositions. In particular it concerns compositions and compounds having activity in in vitro tests on Human Immunodeficiency Virus-infected cells.

The disease known as Acquired Immune Deficiency Syndrome (AIDS) caused by infection by HIV has attracted immense research effort because of the effects of the disease on infected individuals and the dangers of the disease spreading to a wider section of the population. In general, although various chemo-therapeutic treatments have been advocated, and some compounds have emerged as a potential basis for treatment, there is still a need for alternatives. In particular, most treatments such as the compound known as AZT have a high toxicity to cells, and it would be desirable to find compounds which are less toxic. In man, the development of resistance to AZT has been identified as an additional clinical problem.

We have found a group of compounds which show protective properties in vitro screens of cells challenged with HIV-1 and/or HIV-2, and are therefore useful for the treatment of AIDS and AIDS Related Complex and other vital and especially retrovital infections. Accordingly, the present invention provides the use of compounds defined below, in phamaceutical compositions for treating HIV-infected patients. The invention further provides pharmaceutical compositions comprising a said compound in combination or association with a pharmaceutically acceptable diluent or excipient, for the treatment of HIV-infected patents. The invention may also be defined as the use of a said compound for the manufacture of a medicament for the treatment of HIV-infected patients. The invention further provides a process for the production of a pharmaceutical composition for the treatment of a HIV-infected patient, comprising the combination of a compound as defined below with a pharmaceutically acceptable diluent or excipient, and formulating said composition into a form suitable far administration to said patient. The invention also provides a method of treatment of an HIV-infected patient, comprising administering to said patient an effective dose of a said compound. It is to be understood that treatment includes prophylactic treatment of patients at risk, in view of the protective properties observed. The use of the compounds may also be stated as a method of treating HIV-infected or HIV-challenged human cells to prevent or modulate the multiplication of the HIV, comprising administering to said cells an effective dose of a said compound. Whilst this description is especially directed to combating HIV, this invention includes other aspects in which other diseases may be treated, including for example microbial infections.

A 2,2'-dimer of cyclam has been reported as being isolated as a 2% by-product in the synthesis of cyclam (1,4,8, 11-tetraaza-cyclotetradecane) (Barefield et al, J C S Chem Con (1981), 302). This compound was stated to be insoluble in water. We believe that the insoluble 2,2'-bicyclam is a mixture of the 2R,2'R and 2S,2'S enantiomers; we have characterised a soluble dimer which we believe to be the me, so 2R,2'S isomer. The 6,6'-bicyclam isomer has been reported by Fabbrizzi et al, Inorg Chem 25, 2671 (1986). Certain N,N'-linked bicyclic compounds have been reported by Ciampolini et al, Inorg Chem 26, 3527 (1987). No biological activity has been suggested for such compounds.

U.S. Pat. No. 4,156,683 discloses monocyclic and bicyclic macrocyclic compounds, which [axe] *are* said to have biological activity in regulating sodium, potassium and calcium levels in mammals. Additionally, a specific group of N-alkylated monocyclic compounds are said to possess activity against $A_2$ influenza viruses in a modified Hermann test on chick fibroblast tissue. It is also said that the preferred compounds, which form complexes of greater stability, are those having three bridging chains between bridgehead nitrogen atoms, that is fused bicyclic compounds.

EP-A-0296522 discloses certain functionally modified cyclic polyamines, including that known as "cyclam", which complexes with rhodium and may be bound to an antibody or antibody fragment The aromatic-linked cyclic polyamines which form the subject of the present invention are not disclosed, nor is any anti-vital activity.

EP-A-0305320 also discloses several modified cyclic polyamines, but does not disclose identical cyclic polyamines linked together.

WO-A-9105762 discloses polyamines useful for their multi-point chelating activity, but does not disclose linked cyclic polyamines.

WO-A-9216494 is in the same name as the present applicants, and discloses long-chain polyamines, optionally linked to a cyclic polyamine, as agents active against HIV. No molecules having two cyclic polyamines, linked through an aromatic linker are disclosed in this prior art.

Our U.S. Pat. No. 5,021,409 (equivalent to EP-A-0434385) describes linked cyclic compounds as being active against HIV-1 and HIV-2 in in vitro tests. We have now discovered that certain of the linked cyclic compounds exhibit surprisingly improved activity against HIV. Thus, the present invention concerns a selected group of the compounds taught in said USP, having activity of at least an order of magnitude greater than the compounds tested in said USP.

The present invention provides as active compounds linked cyclic compounds of the general formula I $$Z\text{-}R\text{-}A\text{-}R'\text{-}Y \qquad (I)$$

in which Z and Y are identical cyclic polyamine moieties having from 9 to 20 ring members and from 3 to 6 amine nitrogens in the ring spaced by 2 or more carbon atoms from each other, A is an aromatic or heteroaromatic moiety other than quinoline, and R and R' are each methylene linked to an amine nitrogen atom in Z and in Y, the amine nitrogens being otherwise unsubstituted. The invention also encompasses acid addition salts and metal complexes of the compounds of formula I.

In the above formula, the cyclic polyamine moieties may be substituted or unsubstituted, and suitable substituents are alkyl and/or aryl groups, eg of up to 10 carbon atoms, and any other atoms or groups which do not substantially adversely affect the activity or toxicity of the compounds. Preferred moieties are those of 10 to 15 ring members, and there are preferably 3 or 4 amine nitrogen atoms.

The aromatic or heteroaromatic moiety A tethers Y and Z through the linking groups R and R'. Moiety A may be phenyl or fused aromatic such as napthyl, heterocyclic such as pyridyl or thiophenyl, fused heterocyclic or joined aromatic and/or joined heteroaromatic, for example biphenyl or bipyridyl respectively. The moieties A may also be substituted at single or multiple non-linking positions with electron-donating groups, eg alkyl, thio, thioalkyl, hydroxyl, alkoxyl, amino and derivatives thereof, or electron-withdrawing groups or atoms, eg nitro, halogen, carboxy, carboxamido, sulfonic acid and derivatives thereof.

The invention also includes what may be termed "prodrugs", that is protected forms of the linked cyclic compounds, which release the compound after administration to a patient. For example, the compound may carry a protective group which is split off by hydrolysis in body fluids, [eg] *e.g.* in the bloodstream, thus releasing active compound. A discussion of pro-drugs may be found in "Smith and Williams' Introduction to the Principles of Drug Design", H. J. Smith, Wright, 2nd Edition, London 1988.

A few of the active compounds according to the invention [axe] *are* known, (see Inorg Chem 26 (1987), p 3527–3533 and J Chem Soc, Chem Commun, (1991), 206, 207).

Accordingly, certain of the compounds of formula I are novel. The invention accordingly provides novel linked cyclic polyamine compounds of general formula Ia, Z-R-A'-R'-Y (Ia)

in which Z, Y, R and R' are as defined above, with R and R' linked to nitrogen atoms in Z and Y, and A' is an aromatic or heteroaromatic moiety which is unsubstituted or substituted, other than quinoline, provided that A' is not unsubstituted phenylene when Z and Y are 14-membered tetraaza rings, and their acid addition salts and metal complexes.

The invention further provides a method for the production of the compounds of formula la, which method comprises nucleophilic attack by cyclic polyamines Z' and Y' each having a single unprotected ring amine nitrogen, all other ring amine nitrogens being protected, on a compound of formula II

X-R-A'-R'-X II wherein R, R' and A' are as defined above, and each X is an active substituent which can be displaced by the unprotected amine nitrogens of polyamines Z' and Y' and is preferably selected from Br, Cl, I, methanesulfonate, 4-tolylsulfonate and trifluoromethane sulfonate, and subsequently deprotecting the ring amine nitrogens.

It is well within the capabilities and knowledge of the skilled synthetic chemist to protect the amine nitrogens of cyclic polyamines, and it is preferred to use substitution by methanesulfonyl and/or 4-talylsulfonyl and/or diethylphosphoryl. The compounds of formula II are known.

The reaction is preferably carried out by reacting two equivalents of the protected polyamine with the compound of formula II in a solvent, such as acetonitrile or dimethylformamide, tetrahydrofuran or dioxane and in the presence of a base, for example sodium carbonate or potassium carbonate. The reaction generally takes place readily at room temperature to elevated temperature, to give a linked molecule having protected amine nitrogen atoms. In general, a mixture of products will be obtained, and we have found that chromatography on silica gel is a particularly convenient method of separation.

The deprotection step is suitably carried out by refluxing the protected molecule in a mixture of aqueous HBr and acetic acid or in the case of diethylphosphoryl in the presence of hydrogen chloride (gas) in THF or dioxane.

The compounds are indicated for the treatment of vital infections, especially retrovirus infections and particularly HIV infections, and the compounds of formula I are to [he] *be* considered as active compounds for the pharmaceutical compositions, processes for making the same and methods of treatment mentioned above. In these aspects of the invention, it is to be understood that meso forms, enantiomers and resolved optically active forms of the compounds of formula I are included. Also, it is to [he] *be* considered within the invention, compounds of formula I diluted with non-toxic or other active substances.

Acid addition salts, for example hydrochlorides, and non-toxic labile metal complexes of the compounds of formula I are also active compounds according to the present invention. Non-toxic in the present context has to be considered with reference to the prognosis for the infected patient without treatment. Copper and zinc complexes are preferred although other metals such as nickel may be considered, whereas less labile metal atoms such as cobalt and rhodium are less preferred because of likely lower selectivity.

The present invention will now be illustrated by the following preparative examples.

EXAMPLE 1 a) 2,3,5,6- Tetrafluoro-p-xylene-∝,∝'-diol

To a stirred solution of perfluoroterephthalic acid (1.0 g, 4.2 mmol) in anhydrous THF (10 ml) under an atmosphere of dry argon was added Borane. THF complex (1.0M solution in THF, 10 equivalents, 42 ml) dropwise, and the mixture stirred at room temperature overnight. The solution was evaporated under reduced pressure to give a colourless oil and the excess Borane destroyed by addition of anhydrous methanol (40 ml) and evaporation (repeated three times). The residue was treated with 5% aqueous hydrocMoric acid then the pH of the mixture was adjusted to pH9 with 1N aqueous sodium hydroxide solution and extracted with dichloromethane (3×50 ml). The combined organic extracts were dried ($MgSO_4$) and evaporated to give 2,3,5,6-tetrafluoro-p-xylene-∝,∝'-diol (0.75 g, 86%) as a white solid. This was used without further purification.

b) 2,3,5,6- Tetrafluoro-p-xylene-∝,∝'-diol dimesylate

To a stirred solution of 2,3,5,6-tetrafluoro-p-xylene-∝,∝'-diol (0.72 g, 3.4 mmol) in dichloromethane (40 ml) containing triethylamine (1.2 ml, 2.5 equivalents) was added methanesulfonyl chloride (0.58 ml, 2.2 equivalents) dropwise at 0° C. and the mixture was allowed to warm to room temperature overnight. The solution was washed with saturated aqueous sodium bicarbonate solution (2×20 ml) and brine (2×20 ml) then dried ($MgSO_4$) and evaporated under reduced pressure. The residue was suspended in ether and filtered giving 2,3,5,6-tetrafluoro-p-xylene-∝,∝'-diol dimesylate (0.9 g, 72%) as a white solid.

c) 1,1'-[2,3,5,6-Tetrafluoro-1,4-phenylenebis-(methylene)]-bis-tris(p-toluenesulfonyl)-1,4,8,11-tetraazacyclotetradecane 2,3,5,6-Tetrafluoro-p-xylene-∝,∝'-diol dimesylate (150 mg, 0.4 mmol), tris-(p-toluenesulfonyl)-1,4,8,11-tetraazacyclotetradecane monohydrate 826 mg, 1.2 mmol, 3.0 equivalents) and potassium carbonate (252 mg, 3.0 equivalents) in anhydrous acetonitrile (20 ml) were heated to reflux with stirring under argon for 48 hours until all the dimesylate starting material had been consumed; confirmed by TLC (silica gel, 2% methanol in dichloromethane as eluent). The mixture was evaporated under reduced pressure and the residue was dissolved in ethyl acetate (40 ml) and washed with saturated aqueous sodium bicarbonate solution (2×20 ml) and brine (2×20 ml) then dried ($MgSO_4$) and evaporated. The residue was purified by column chromatography on silica gel during with 2% methanol in dichloromethane giving a white foam identified by $^1H$ NMR and FAB-MS as 1,1'-[2,3,5,6-tetrafluoro-1,4-phenylene-bis-(methylene)]-bis-tris-(p-toluenesulfonyl)-1,4,8,11-tetraazacyclotetradecane $C_{70}H_{86}N_8O_{12}S_6F_4$ requires C, 56.05; H, 5.78; N, 7.47; found C, 55.81; H, 5.73; N, 7.36.

d) 1,1'-[2,3,5,6-Tetrafluoro-1,4-phenylenebis-(methylene)]-bis-1,4,8,11-tetraazacyclotetradecane 1,1'-[2,3,5,6-Tetrafluoro-1,4-phenylenebis-(methylene)]-bis-tris-(p-toluenesulfonyl)-1,4,8,11-tetraazacyclotetradecane (200 mg, 0.13 mmol) was dissolved in a mixture of acetic acid and hydrobromic acid (48%) in a ratio of approximately 3:2 by volume (10 ml) and heated to 100° C. for 24 hours during which time a white solid precipitated. The mixture was allowed to cool and the solid was filtered off and washed with acetic acid and ether and dried in vacuo giving a white solid identified by $^1H$ NMR, FAB-MS and elemental analysis as 1,1'-[2,-3,5,6-tetra-fluoro-1,4-phenylene-bis-(methylene)]-bis-1,4,8,11-tetraazacyclo-tetradecane octahydrobromide dihydrate (65 mg, 40%).

$C_{28}H_{62}N_8O_2Br_8F_4$ requires C, 26.73; H, 4.96; N, 8.90; found C, 26.84; H, 5.05; N, 8.21.

The following compounds were prepared using analogous methods to those described above in steps b)-d):

5-Nitro-m-xylene∝,∝'-diol gave 1,1-[5-Nitro-1,3-phenylene-bis-(methylene)]-bis-1,4,8,11-tetraazacyclotetradecane octahydrobromide dihydrate. $C_{28}H_{65}N_9O_4Br_8$ requires C, 27.31; H, 5.31; N, 10.24; found C, 27.49;, H, 5.26; N, 9.75.

2,4,5,6-Tetrachloro-m-xylene-∝,∝'-diol gave 1,1'-[2,4,5,6-tetrachloro-1,3-phenylene-bis-(methylene)]-bis-1,4,8,11-tetraaza-cyclotetradecane octahyclrobromide dihydrate.

$C_{28}H_{62}O_2Cl_4Br_8$, requires C, 25.40; H, 4.71; N, 8.46; found C, 25.72; H, 4.76; N, 8.05.

EXAMPLE 2 a) ∝,∝'-Dibromo-1,4-dimethylnaphthalene

To a solution of 1,4-dimethylnaphthalene (0.5 g, 3.2 mmol) and benzoyl peroxide (0.08 equivalents, 62 mg) in carbon tetrachloride (20 ml) was added N-bromosuccinimide (1.14 g, 2.0 equivalents) and the mixture was heated to reflux for 24 hours during which time a white solid precipitated. The mixture was faltered hot (to remove the succinimide by-product) and then allowed to cool over several hours during which time a white cystalline solid precipitated. The solid was filtered off and dried giving 1,4-dimethylnaphthalene-∝,∝'-dibromide (473 mg, 50%).

The following compound was prepared using methods analogous to steps c) and d) of Example 1:

1,4-Dimethylnaphthalene-4,4'-dibromide gave 1,1'-[1,4-naphthylenebis-(methylene)]-bis-1,4,8,11-tetraazacyclotetradecane octahydrobromide tetrahydrate.

$C_{32}H_{72}N_8O_4Br_8$ requires C, 30.20; H, 5.69;, N, 8.81; found C, 30.28; H, 5.52; N, 8.66.

EXAMPLE 3 a) 1-Benzyl-5,13-di-(p-toluenesulfonyl)-9-methanesulfonyl-1,5,9,13-tetraazacyclohexadecane.

To a solution of N,N-bis-[3-(p-toluenesulfonylamidopropyl)-]benzylamine hydrochloride (25 g) (NL Patent 6603655) in dry DMF (800 ml) under argon was added sodium hydride (10 equivalents) in small portions over 3 hours. When the addition was complete the solution was heated at 6° C. for 1 hour then allowed to cool and the excess sodium hydride was removed by filtration under argon. The filtrate was transferred to another dry flask and the solution was then heated to 100°–110° C. and bis-propanolamine-trimethanesulfonate [P Moore, J Chem Soc Dalton Trans 1985 (7) 1361–1364] (1.0 equivalent) in DMF (500 ml) was added dropwise over 8 hours with rapid stirring. The temperature was maintained at 100°–110° C. for a further 16 hours, allowed to cool then the mixture was poured into iced water (1500 ml) and the resulting off-white precipitate that formed was collected by filtration. The solid was dissolved in dichloromethane (250 ml) and the solution was washed with water (5×50 ml), then dried ($MgSO_4$) and evaporated under reduced pressure to give a yellow oil. Trituration with ethanol (200 ml) gave a white crystalline solid which was filtered off, washed with a small volume of ethanol, then ether and dried in vacuo to give 1-benzyl-5,-13-di-(p-toluenesulphonyl)-9-methanesulphonyl-1,5,9,-13tetraazacyclohexadecane (45%), identified by $^1H$ NMR and FAB-MS.

b) 1,9-Di-(p-toluenesulfonyl)-5-methanesulfonyl-1,5,9,13-tetraazacyciohexadecane To a solution of 1-benzyl-5,13-di-(p-toluene-sulfonyl)-9-methanesulfonyl-1,5,9,13-tetraazacyclohexadecane in formic acid (20 ml) was added Palladium hydroxide on carbon (Pearlmans catalyst, 4.0 g) and the resulting suspension was heated to reflux for 72 hours with stirring. The mixture was allowed to cool, then filtered through celite and the filtrate was evaporated under reduced pressure. The colourless oil which remained was dissolved in dichloromethane (50 ml) and washed with 10% aqueous sodium hydroxide solution (2×20 ml), and water (2×20 ml) then dried ($MgSO_4$) and evaporated under reduced pressure. The residue was purified by column chromatography on silica gel eluting with 3% methanol in dichloromethane giving a white solid identified by $^1H$ NMR and FAB-MS as 1,9-di-(p-toluenesulphonyl-5-methanesulfonyl-1,5,9,13-tetraaza-cyclohexadecane.

The mono-deprotected tetraazacyclohexadecane macrocycle described in step b) was used as described in Example 1 steps c) and d), to prepare tetraazacyclohexadecane dimers.

The following compounds were prepared in this manner.

4,4'-Dibromo-m-xylene gave 1,1'-[1,3-phenylene-bis-(methylene)]-bis-1,5,9,13-tetraazacyclohexadecane octahydrobromide hexahydrate.

$C_{32}H_{72}N_8O_6Br_8$ requires C, 29.2; H, 6.15; N; 8.54; found C, 29.37; H, 5.50; N, 7.90.

4,4'-Dibromo-p-xylenegave 1,1'-[1,4-phenylene-bis-(methylene)]-bis-1,5,9,13-tetraazacyclohexadecane octahydrobromide hexahydrate.

$C_{32}H_{76}N_8O_6Br_8$ requires C, 29.29; H, 6.15; N, 8.54; found. C, 28.96; H, 5,47; N,7.96.

Other compounds which may be made according to the invention are:

1,1'-[1,3-phenylenebis(methylene)]-bis-1,5,9,13-tetraazacyclohexadecane 1,1'-[1,3-phenylenebis(methylene)]-bis-1,5,9-triazacyclododecane 1,1'-[1,4-phenylenebis(methylene)]-bis-1,5,9-triazacyclododecane

EXAMPLE 4

Synthesis of Compound F 1,1'-[1,4-Phenylene-bis-(methylene)]-bis-1,4,8,11-tetraazacyclotetradecane zinc dichloride monohydrate To a stirred solution of 1,1'-[1,4-phenylene-bis-(methylene)]-bis-1,4,8,11-tetraazaeyclotetradecane (1 g) in methanol (25 ml) was added zinc(II) chloride (0.54 g, 2.0 eq) in methanol (5 ml). Towards the end of the addition a white precipitate formed. Sufficient methanol and water were added to give a homogenous solution and the mixture was then evaporated in vacuo. The solid residue was suspended in a mixture of methanol/ether and filtered giving 1,1'-[1,4-phenylene-bis-(methylene)]-bis-1,4,8,11-tetraazacyclotetradecane zinc dichloride monohydrate (1.45 g, 94%) as a white powder.

$C_{28}H_{56}Cl_4OZn_2$ requires; C, 42.38; H, 7.11; N, 14.12; Cl, 17.88: found; C, 42.64; H, 7.14; N, 14.18; Cl, 17.89.

EXAMPLE 5

Synthesis of Compound G 1,1'-[1,4-Phenylene-bis-(methylene)]-bis-1,4,8,11-tetraazacyclotetradecane copper diacetate hexahydrate To a stirred solution of 1,1'[1,4-phenylene-bis-(methylene)]-bis-1,4,8,11-tetraazacyclotetradecane (100 mg) was added copper(II) acetate (72 mg, 2.0 eq) in one portion. The solution became dark blue/purple in colour almost immediately. The mixture was stirred for one hour then triturated with ether to give a blue precipitate. The blue solid was filtered off and dried giving 1,1'-[1,4-phenylene-bis-(methylene)]-bis-1,4,8,11-tetraazacyclotetradecane copper diacetate hexahydrate (80 mg, 46%).

$C_{36}H_{80}N_8O_{Cu2}$ requires; C, 43.58; H, 8.13; N, 11.29; found: C, 43.24; H, 7.88; N, 11.13.

EXAMPLE 6

1,1'-[3'-Biphenylene-bis-(methylene)]-bis-tris-(p-toluenesulphonyl)-1,4,8,11tetraazacyclotetradecane A mixture of 3,3'-bis-(bromomethyl)-1,1'-biphenyl [W. Wenner, J. Org. Chem. (1952), 17, 525–528], (200 mg, 0.59 mmol), anhydrous potassium carbonate (325 mg, 2.35 mmol, 4 eq) and tris-(p-toluene-sulphonyl)-1,4,8,11-tetraazacyclotetradecane (801 mg, 1.18 mmol, 2 eq) in anhydrous acetonitrile (15 ml) was stirred at 50° C. under argon. After 6 hours the reaction mixture was allowed to cool; dichloromethane (75 ml) was added and the resulting solution filtered. The filtrate was evaporated in vacuo to yield a glassy white solid. Chromatography of the crude product on a column of silica gel (2.5 cm×20 cm), eluting with methanol/dichloromethane 1:160 v/v gave a white solid, identified by $^1$H NMR as 1,1'-[3,3'-biphenylene-bis-(methylene)]-bis-tris-(p-toluenesulphonyl)-1,4,8,11-tetraazacyclotetradecane (665 mg, 76%).

Synthesis of Compound J 1,1'-[3,3'-Biphenylene-bis-(methylene)]-bis-1,4,8,11-tetraazacyclotetradecane octahydrobromide tetrahydrate The per-tosylated derivative from above (450 mg, 0.30 mmol) was dissolved in glacial acetic acid (9 ml). Hydrobromic acid (~48% w/v, Aldrich, 3.5 ml) was added and the resulting mixture heated to reflux. After 24 hours the dark brown solution was cooled in an ice bath over 2 hours during which time an off-white precipitate formed. The precipitate was collected by centrifugation and washed with glacial acetic acid (3×10 ml) followed by diethyl ether (4×10 ml) then dried overnight in vacuo to give a white powder, identified by $^1$H NMR and elemental analysis as 1,1'-[3,3'-biphenylene-bis-(methylene)]-bis-1,4,8,11-tetraazacyclotetradecane octahydrobromide tetrahydrate (194 mg, 50%). $C_{34}H_{74}N_8Br_8O_4$ requires; C, 31.46; H, 5.70; N, 8.63; found; C, 31.30; H, 5.68; N, 8.60.

EXAMPLE 7

1,1'-[4,4'-(2,2'-Bipyridine)-bis-(methylene)]-bis-tris-(p-toluenesulphonyl)-1,4,8,11-tetraazacydotetradecane A mixture of 4,4'-bis-(bromomethyl)-2,2'-bipyridine [T J Meyer, Inorg. Clam. (1991), 30, 2942–2949], (200 mg, 0.57 mol), anhydrous potassium carbonate (314 mg, 2.27 mmol, 4 eq) and tris-(p-toluenesulfonyl)-1,4,8,11-tetraazacyclotetradecane (774 mg, 1.14 mmol, 2 eq) in anhydrous acetonitrile (20 ml) was stirred at 50° C. under argon for 2 hours. The mixture was allowed to cool and dichloromethane (100 ml) was added and the resulting solution filtered through celite. The filtrate was evaporated in vacuo to give a yellow glassy solid which was purified by column chromatography on silica gel (3×20 cm column) using triethylamine/methanol/dichloromethane 1:1:100 v/v as eluent. A glassy white solid was obtained, identified by $^1$H NMR as 1,1'-[4,4'-(2,2'-bipyridine)-bis-(methylene)]-bis-tris-(p-toluenesulphonyl)-1,4,8,11-tetraazacyclotetradecane (600 mg, 70%).

Synthesis of Compound K 1,1'-[4,4'-(2,2'-Bipyridine)-bis-(methyl)]-bis-1,4,8,11-tetraazacyclotetradecane decahydrobromide pentahydrate The per-tosylate derivative from above (570 mg, 0.38 mmol) was dissolved in glacial acetic acid (6.5 ml). Hydrobromic acid (~48% w/v, Aldrich, 3.0 mmol) was added and the mixture heated to reflux for 24 hours. The resulting dark brown solution was cooled in an ice bath over 2 hours) during which time an off-white precipitate formed. The precipitate was collected by centrifugation and washed with glacial acetic acid (3×10 ml) followed by diethyl ether (5×10 ml) and dried overnight in vacuo to give a white powder identified by $^1$H NMR and elemental analysis as 1,1'-[4,4'-(2,2'-bipyridine)-bis-(methylene)]-bis-1,4,8,11-tetraazacyclotetradecane decahydrobromide pentahydrate (450 mg, 81%).

$C_{32}H_{76}N_{10}Br_{10}O_5$ requires; C, 25.97; H, 5.17; N, 9.46; found; C, 26.07; H, 4.57; N, 9.47.

EXAMPLE 8

1,1'-[2,9-(1,10-Phenanthroline)-bis-(methylene)]-bis-tris-(p-toluenesulphonyl)-1,4,8,11-tetraazacyclotetradecane A mixture of 2,9-bis-(bromomethyl)-1,10-phenanthroline [C J Chandler, J. Heterocycl. Chem. (1981), 18, 599–601], (200 mg, 0.54 mmol), anhydrous potassium carbonate (300 mg,. 2.17 mmol, 4 eq) and axis-(p-toluenesulphonyl)-1,4,8,11-tetraazacyclotetradecane (740 mg, 1.09 mmol, 2 eq) in anhydrous acetonitrile (20 ml) were stirred at 50° C. under argon for 3 hours. The mixture was allowed to cool and dichloromethane (100 ml) was added and the resulting solution filtered through celite. The filtrate was evaporated in vacuo to give a yellow glassy solid which was purified by column chromatography on silica gel (3×2 cm column) using triethylamine/methanol/dichloromethane 1:3:100 v/v eluent. A pale yellow solid was obtained, identified by $^1$H NMP as 1,1'-[2,9-(1,10-phenamhroline)-bis-(methylene)]-bis-tris-(p-toluenesulphonyl)-1,4,8,11-tetraazacyclotetradecane (575 mg, 69%).

Synthesis of Compound L 1,1'-[2,9-(1,10-Phenanthroline)-bis-(methylene)]-bis-1,4,8,11-tetraazacyclotetradecane decahydrobromide trihydrate The per-tosylated derivative from above (400 mg, 0.26 mmol) was dissolved in glacial acetic acid (8 ml). Hydrobromic acid (48% w/v, Aldrich, 3.5 ml) was added and the mixture was heated to reflux for 16 hours. The resulting dark brown solution was cooled in an ice bath over 2 hours during which time an off-white precipitate formed. The precipitate was collected by centrifugation then purified by re-precipitation from a mixture of hydrobromic acid (~48% w/v, 2 ml) and water (2 ml) with glacial acetic acid (5 ml). The white solid was again collected by centrifugation, washed with glacial acetic acid (3×10 ml) and diethyl ether (4×10 ml) and finally dried overnight in vacuo to give a white powder, identified by $^1$H NMR and elemental analysis as 1,1'-[2,9-(1,10-phenanthroline)-bis-(methylene)]-bis-1,4,8,11-tetraazacyclotetradecane decahydrobromide trihydrate (80 mg, 21%).

$C_{34}H_{72}N_{10}Br_{10}O_3$ requires; C, 27.82; H, 4.94; N, 9.54; found; C, 27.81; H, 4.97; N, 9.17.

EXAMPLE 9

This compound and corresponding intermediates axe described by T. A. Kaden, Helv. Chim. Acta., (1985), 69, 53–61. An alternative procedure is given below.

11,11'-[1,4-Phenylene-bis-(methylene)]-bis-tris-(p-toluenesulphonyl)-1,4,7,11-tetraazacyclotetradecane A mixture of α,α'-dibromo-p-xylene (249 mg, 0.94 mmol), anhydrous potassium carbonate (652 mg, 4.71 mmol, 5 eq) and tris(p-toluenesulphonyl)-1,4,7,11-tetraazacyclotetradecane [T. A. Kaden, Heir. Chim. Acta., (1983), 66, 861–870] (1.25 g, 1.89 mmol, 2 eq) in anhydrous acetonitrile (15 ml) was heated at 50° C. with stirring under argon for 18 hours. The reaction mixture was allowed to cool and dichloromethane (50 ml) was added and the resulting solution filtered through celite. The filtrate was evaporated in vacuo to give a white foam which was purified by column chromatography on silica gel using methanol/dichloromethane (1:40 v/v) as eluent. A white solid was obtained, identified by $^1$H NMR as 11,11'-[1,4-phenylene-bis-(methylene)]-bis-tris-(p-toluenesulphonyl)-1,4,7,11-tetraazacyclotetradecane (1.0 g, 74%)

Synthesis of Compound M 11,11'-[1,4-Phenylene-bis-(methylene)]-bis-1,4,7,11-tetraazacyclotetradecane octahydrobromide dihydrate The per-tosylated derivative from above (500 mg, 0.35 mmol) was dissolved in glacial acetic acid (7 ml). Hydrobromic acid (~48% w/v, 4 ml) was added and the resulting mixture heated to reflux for 20 hours. Further glacial are fie acid (10 ml) was added and the solution was cooled in an ice bath over 1 hour during which time a white precipitate formed. The solid was collected by centrifugation and washed with glacial acetic acid (2×10 ml) followed by diethyl ether (4×10 ml) and dried overnight in vacuo to give a white powder, identified by $^1$H NMR and elemental analysis as 11,11'-[1,4-phenylene-bis-(methylene)]-bis-1,4,7,11-tetraazacyclotetradecane octahydrobromide dihydrate (280 mg, 67%).

$C_{28}H_{66}N_8Br_8O_2$ requires; C, 28.35; H, 5.61; N, 9.45; found; C, 28.34; H, 5.42; N, 9.02.

EXAMPLE 10

11[(1, Methylene-4-bromomethylene)-phenylene]-tris-(p-toluenesulphonyl)-1,4,7,11-tetraazacyclotetradecane A mixture of α,α'-dibromo-p-xylene (3.98 g, 15.1 mmol, 10 eq), and anhydrous potassium carbonate (417 mg, 3.02 mmol, 2 eq) in anhydrous acetonitrile (20 ml) was heated to 50° C. With rapid stirring a solution of tris-(p-toluenesulphonyl)-1,4,7,11-tetraazacyclotetradecane (1.0 g, 1.51 mmol) in anhydrous acetonitrile (20 ml) was added dropwise over 4 hours. After a further 1 hour the reaction mixture was allowed to cool and the solvent evaporated in vacuo. The residue was purified by column chromatography on silica gel (5×20 cm), eluting with a gradient of dichloromethane to methanol/dichloromethane 1:20 v/v over 2 liters total elution volume. To the resulting colourless glass was added dry hexane (150 ml) and the mixture was heated to reflux then allowed to cool to room temperature. The precipitate which formed was filtered, washed with hexane (3×10 ml) followed by diethyl ether (20 ml) and dried overnight in vacuo to give the title compound as a white powder (710 mg, 53%).

1,11'-[1,4-Phenylene-bis-(methylene)]-tris-(p-tohenesulphonyl)-1,4,8,11-tetraazacyclotetradecane)-tris-(p-toluenesulphonyl)-1,4,7,11-tetraazacyclotetradecane A mixture of 11-[(1-methylene-4-bromomethylene)-phenylene]-tris-(p-tohenesulphonyl)-1,4,7,11-tetraacyclotetradecane (350 mg, 0.41 mmol), anhydrous potassium carbonate (230 mg, 1.66 mmol, 4 eq) and tris-(p-toluenesulphonyl)-1,4,8,11-tetraazacyclotetradecane (422 mg, 0.62 mmol, 1.5 eq) in anhydrous acetonitrile (20 ml) were heated with stirring at 50° C. under argon for 7 hours. The reaction mixture was allowed to cool and the solvent was evaporated in vacuo. The residue was purified by column chromatography on silica gel (2.5×25 cm column) using methanol/dichloromethane (1:60 v/v) as eluent, followed by preparative thin layer chromatography on silica gel (eluent methanol/dichloromethane 1:40 v/v, 20 mg/plate) to give a colourless glass, identified by $^1$H NMR as the title compound (130 mg, 30%).

Synthesis of Compound N 1,11'-[1,4-Phenylene-bis-(methylene)]-1,4,8,11-tetraazacyclotetradecane-1,4,7,11-tetraazacydotetradecane octahydrobromide hexahydrate The per-tosylated derivative from above (115 mg, 0.08 mmol) was dissolved in glacial acetic acid (3 ml). Hydrobromic acid (~48%, Aldrich, 1.5 mmol) was added and the mixture was heated to reflux for 48 hour. The resulting dark brown solution was cooled in an ice bath and a white precipitate formed. The solid was collected by centrifugation and washed with glacial acetic acid (3×10 ml) followed by diethyl ether (5×10 ml) and dried overnight in vacuo to give a white powder, identified by $^1$H NMR and elemental analysis as 1,11'-[1,4-phenylene-bis-(methylene)]-1,4,8,11-tetraazacyclotetradecane-1,4,7,11-tetraaza-cyclotetradecane octahydrobromide hexahydrate. (71 mg, 75%). $C_{29}H_{74}N_8Br_8O_6$ requires; C, 26.73; H, 5.93; N, 8.91; found; C, 26.50; H. 5.69; N, 9.31.

EXAMPLE 11

1,1'-[2,6-Pyridinebis-(methylene)]-bis-tris-(p-toluenesulphonyl)-1,4,8,11-tetraazacyclotetradecane A stirred solution of 2,6-bis(bromomethyl)pyridine hydrobromide [M. E. Haeg, B. J. Whitlock and H. W. Whitlock Jr, J. Ant. Chem. Soc., (1989), 111, 692], (131 mg, 0.378 mmol), tris-(p-toluene-sulphonyl)-1,4,8,11-tetraazacyclotetradecane (500 mg, 0.75 mmol) and potassium carbonate (400 mg, 2.88 mmol) in anhydrous acetonitrile (15 ml) was heated at 80° C. for 22 hours under an atmosphere of arson. The reaction mixture was allowed to cool to room temperature and concentrated in vacuo. The residue was purified by column chromatography on silica gel using 3% methanol in dichloromethane as eluent thus affording a pale white solid which was identified by $^{1}$H NMP, and FAB-MS as 1,1'-[2,6-pyridinebis-(methylene)]-bis-tris(p-toluene-sulphonyl)-1,4,8,11-tetraacyclotetradecane (500 ml, 93%).

Mass spectrum (FAB); m/e (relative intensity); 1428 (M+1, 100), 1272 (35)

Synthesis of Compound O 1,1'-[2,6-Pyridinebis-(methylene)]-bis-1,4,8,11-tetraazacyclotetradecane octahydrobromide tetrahydrate To a stirred solution of 1,1'-[2,6-pyridinebis-(methylene)]-bis-tris(p-toluenesulphonyl)-1,4,8,11-tetraazacyclotetradecane (500 mg, 0.35 mmol) in acetic acid (16 ml) was added 48% hydrobromic add (12 ml) and the solution heated to 110° C. for 48 hours during which time a white solid precipitated. The reaction mixture was allowed to cool to mom temperature and the solid was filtered off, washed with acetic acid followed by ether and dried in vacuo thus affording a white solid which was identified by $^{1}$H NMR, $^{13}$C NMR, FAB-MS and elemental analysis as 1,1'-[2,6-pyridinebis-(methylene)]-bis-1,4,8,11-tetraazacyclotetradecane octahydrobromide tetrahydrate (230 mg, 65%).

$C_{27}H_{69}N_9O_4Br_8$ requires; C, 26.50; H, 5.64; N, 10.31; Br, 52.29; found C, 26.91; H, 5.31; N, 10.08; Br, 51.99. Mass spectrum (FAB); m/e (relative intensity); 586 (M+HBr, 48), 584 (M+HBr, 50), 504 (M+1, 100), 201 (60).

EXAMPLE 12

1,1'-[3,5-Pyridine-bis-(methylene)]-bis-tris(p-toluenesulphonyl)-1,4,8,11-tetraazacyclotetradecane A stirred solution of 3.5-bis(bromomethyl)pyridine hydrobromide (M. Momenteau, J. Mispelter, B. Loock and J. M. Lhoste, J. Chem. Soc. Perkin Trans. 1, (1985), 61], (131 mg, 0.37 mmol) , tris-(p-toluenesulphonyl)-1,4,8,11-tetraazacyclotetradecane (500 mg, 0.755 mmol) and potassium carbonate (400 mg, 2.88 mmol) in anhydrous dimethylformamide (15 ml) were heated at 70° C. for 21 hours under an atmosphere of argon. The reaction mixture was allowed to cool to room temperature and concentrated in vacuo. The residue was purified by column chromatography on silica gel using 2% methanol in dichloromethane as eluent thus affording a white foamy solid which was identified by $^{1}$H NMR and FAB-MS as 1,1'-[3,5-pyridinebis-(methylene)]-bis-tris(p-toluenesulphonyl)-1,4,8,11-tetraazacyclotetradecane (320 mg, 78%).

Mass spectrum (FAB); m/e (relative intensity); 1428 (M+1, 100), 1272 (45).

Synthesis of Compound P 1,1'[3,5-Pyridinebis-(methylene)]-bis-1,4,8,11-tetraazacyclotetradecane nonahydrobromide dihydrate To a stirred solution of 1,1'-[3,5-pyridinebis-(methylene)-bis-tris(p-tohenesulphonyl)-1,4,8,11-tetraazacyclotetradecane (320 mg, 0.224 mmol) in acetic acid (12 ml) was added 48% hydrobromic acid (8 ml) and the solution heated to 100° C. for 48 hours during which time a white solid precipitated. The reaction mixture was allowed to cool to room temperature and the solid was filtered off, washed with acetic add followed by ether and dried in vacuo thus affording a white solid which was identified by $^{1}$H NMR, $^{13}$C NMR, FAB-MS and elemental analysis as 1,1'-[3,5-pyridinebis-(methylene)]-bis-1,4,8,11-tetraazacyclotetradecane nonahydrobramide dihydrate (150 mg, 53%).

$C_{27}H_{66}N_9O_2Br_9$ requires; C, 25.56; H, 5.21; N, 9.94; Br, 56.74; found C, 25.71; H, 5.25; N, 9.76; Br, 56.28. Mass spectrum (FAB); m/e (relative intensity); 586 (M+HBr, 39), 584 (M+HBr, 41), 504 (M+1, 60), 201 (100).

EXAMPLE 13

1,1'-[1,3-Phenylenebis-(methylene)]-bis-tris(p-toluenesulphonyl)-1,4,7,10-tetraazacyclododecane A stirred solution of α,α'-dibromo-m-xylene (125 mg, 0.472 mmol), tris-(p-tohenesulphonyl)-1,4,7,10-tetraazacyclododecane [M. F. Tweedle et al, Inorg. Chem., (1992), 30, 1265], (600 mg, 0,945 mmol) and potassium carbonate (400 mg, 2.88 mmol) in anhydrous acetonitrile (15 ml) were heated to reflux for 6 hours under an atmosphere of argon. The resulting cloudy white solution was allowed to cool to room temperature and the solids collected by filtration and washed with acetonitrile. The solid residue was dissolved in a mixture of dichloromethane (100 ml) and water (15 ml). The organic phase was separated and washed with water (15 ml), dried ($MgSO_4$) and concentrated under reduced pressure. The residue was dried in vacuo thus affording a white foamy solid which was identified by $^{1}$H NMR as 1,1'-[1,3-phenylenebis-(methylene)]-bis-tris-(p-toluenesulphonyl)-1,4,7,10-tetraazacyclododecane (330 mg, 51%).

Synthesis of Compound Q 1,1'-[1,3-Phenylenebis-(methylene)]-bis-1,4,7,10-tetraazacyclododecane hexahydrobromide To a stirred solution of 1,1'-[1,3-phenylenebis-(methylene)]-bis-tris-(p-toluenesulfonyl)-1,4,7,10-tetraazacyclododecane (330 mg, 0.24 mmol) in anhydrous methanol/tetrahydrofuran (1:2, 15 ml) was added 3% sodium amalgam (20 g) and dibasic sodium phosphate (400 mg). The reaction mixture was vigorously stirred under argon at 70° C. for 41 hours. The reaction mixture was allowed to cool to room temperature and the supernatent solution was separated from the solids by decantation then concentrated in vacuo. Chloroform (50 ml) and water (5 ml) were added to the residue and the aqueous phase was extracted with chloroform (3×50 ml). Concentration of the combined organic fractions afforded quantitatively a viscous oil which was identified by 1H NMR as 1,1'-[1,3-phenylenebis-(methylene)]-bis-1,4,7,10-tetraazacyclododecane.

Into a stirred solution of 1,1'-[1,3-phenylenebis-(methylene)]-bis-1,4,7,10-tetraazacyclododecane in ethanol (20 ml, 95%) was bubbled HBr gas for 15 minutes resulting in an immediate white precipitate. The white solid was filtered off, washed with ethanol and ether and immediately dried in vacuo for 48 hours thus affording a white solid which was identified by $^{1}$H NMR, $^{13}$C NMR, FAB-MS and elemental analysis as 1,1'-[1,3-phenylene-(methylene)]-bis-1,4,7,10-tetraazacyclo-dodecane hexahydrobromide (130 mg, 63%).

$C_{27}H_{52}N_8Br_6$ requires C, 30.92; H, 5.62; N, 12.02; Br, 51.43; found C, 31.09; H, 5.80; N, 11.90; Br, 51.17. Mass spectrum (FAB); m/e (relative intensity); 529 (M+HBr, 53), 527 (M+HBr, 55), 447 (M+I, 100), 277 (40), 185 (35).

EXAMPLE 14

1,1'-[1,4-Phenylenebis-(methylene)]-bis-tris(p-toluenesulphonyl)-1,4,7,10-tetraazacyclododecane A stirred solution of α,α'-dibromo-p-xylene (99 mg, 0.374 mmol), tris-(p-toluenesulphonyl)-1,4,7,10-tetraazacyclododecane (475 mg, 0.748 mmol) and potassium carbonate (320 mg, 2.24 mmol) in anhydrous acetonitrile (15 ml) was heated at reflux for 1.4 hours under an atmosphere of argon. The resulting cloudy white solution was allowed to cool to room temperature and the solids collected by filtration and washed with acetonitrile. The solid residue was dissolved in a mixture of dichloromethane (120 ml) and water (15 ml). The organic phase was separated and washed with water (15 ml), dried ($MgSO_4$) and concentrated under reduced pressure. The residue was dried in vacuo thus affording a white solid which was identified by $^1$H NMR as 1,1'-[1,4-phenylenebis-(methylene)]-bis-tris-(p-toluenesulphonyl)-1,4,7,10-tetraazacyclododecane (360 mg, 70%).

Mass spectrum (FAB); m/e (relative intensity); 1371 (IVI+1, 12), 1217 (8).

Synthesis of Compound R 1,1'-[1,4-Phenylenebis-(methylene)]-bis-1,4,7,10-tetraazacyclododecane hexahydrobromide To a stirred solution of 1,1'-[1,4-phenylenebis-(methylene)-bis-tris(p-toluensulphonyl)-1,4,7,10-tetraazacycledodecane (360 mg, 0.262 mmol) in anhydrous methanol/dimethylsulphoxide (1:5, 18 ml) was added 3% sodium amalgam (23 g) and dibasic sodium phosphate (400 mg). The reaction mixture was vigorously stirred under argon at 100° C. for 4 hours then allowed to cool to room temperature and the supernatent solution was separated from the solids by decantation and concentrated in vacuo. Chloroform (50 ml) and water (5 ml) were added to the residue and the aqueous phase was extracted with chloroform (3×50 ml). Concentration of the combined organic fractions afforded quantitatively a foamy white solid which was identified by $^1$H NMR as 1,1'-[1,4-phenylenebis-(methylene)]-bis-1,4,7,10-tetraazacyclododecane.

Into a stirred solution of 1,1'-[1,4-phenylenebis-(methylene)]-bis-1,4,7,10-tetraazacyclododecane in ethanol (15 ml, 95%) was bubbled HBr gas for 15 minutes resulting in an immediate white precipitate. The white solid was filtered off, washed with ethanol and ether and immediate dried in vacuo for 48 hours thus affording a white solid which was identified by $^1$H NMR, $^{13}$C NMR, FAB-MS and elemental analysis as 1,1'-[1,4-phenylenebis-(methylene)]-bis-1,4,7,10-tetra-azacyclododecane hexahydrobromide (115 mg, 44%).

$C_{27}H_{52}N_8Br_6$ requires C, 30.92; H, 5.62; N, 12.02; Br 51.43, found C, 30.90; H, 5.83; N, 11.83; Br, 51.19. Mass spectrum (FAB); m/e (relative intensity); 529 (M+HBr, 40), 527 (M+HBr, 40), 447 (M+1, 58), 185 (100).

EXAMPLE 15

1,1'-[2,5-Thiophene-bis-(methylene)]-bis-tris-(p-toluenesulphonyl)-1,4,8,11-tetraazacyclotetradecane To a solution of tris-p-toluenesulphonyl-1,4,8,11-tetraazacyclotetradecane monohydrate (1.0 g, 1.5 mmol) and potassium carbonate (300 mg, 2.2 mmol) in acetonitrile (20 ml) was added 2,5-dichloromethyl thiophene [J. M. Griffing, L. F. Salisbury, J. Am. Chem. Soc., (1948), 70, 3416–3419], (137 mg, 0.76 mmol) and the mixture was heated to reflux overnight with rapid stirring. The mixture was allowed to cool and the solid was filtered off. The filtrate was evaporated in vacuo and the residue partitioned between methylene chloride (50 ml) and water (25 ml). The organic layer was separated, dried ($Na_2SO_4$) and evaporated in vacuo to give the crude product as a light brown solid. Column chromatography [silica gel; methylene chloride/methanol(40/1)] was used to isolate a white solid identified by $^1$H NMR and FAB-MS as 1,1'-[2,5-thiophene-bis-(methylene)]-bis-tris-(p-tolueno-sulphonyl)-1,4,8,11-tetraazacyclotetradecane (315 mg, 29% ).

Mass spectrum (FAB); M/e (relative intensity); 1434 (M+1, 49), 1277 (31). 772 (100), 616 (30), 508 (24).

Synthesis of Compound T 1,1'-[2,5-Thophenebis-(methylene)]-bis-1,4,8,11-tetraazacyclotetradecane octahydrobromide To a solution of 1.1'-[2,5-thiophene-bis-(methylene)]-bis-tris-(p-toluenesulphonyl)-1,4,8,11-tetraazacyclotetradecane (177 mg, 0.12 mmol) in acetic acid (6 ml) was added hydrobromic acid (Aldrich 48% aqueous, 4 ml) and the mixture was heated to a reflux with stirring for 16 hours during which time a light brown solid precipitated from a dark brown solution. On cooling, a further portion of acetic acid was added (10 ml) and the solids were filtered off, washed with acetic acid (10 ml) and ether (20 ml) and dried in vacuo giving a white solid identified by $^1$H NMR and FAB-MS as 1,1'-[2,5-thiophene-bis-(methylene)-bis-1,4,8,11-tetraazacyclotetradecane octahyarobromide (82 mg, 97%), Mass spectrum (FAB); m/e (relative intensity); 591 (M+HBr, 26), 589 (M+HBr, 26), 509 (M+1, 22) 311 (23), 201 (71), 185 (100).

The compounds of the invention were tested in a screen by the MTT method (I Vixol Methods 120:309–321 [1988]). MT-4 cells ($2.5\times10^4$/well) were challenged with HIV-1 (HTLV-IIIB) or HIV-2 (LAV-2 ROD) at a concentration of 100 $CCID_{50}$ and incubated in the presence of various concentrations of the test compounds, which were added immediately after challenge with the virus. After 5 days culture at 37° C. in a $CO_2$ incubator, the number of viable cells was assessed by the MTT (tetrazolium) method. Anti-viral activity and cytotoxicity of the compounds are expressed in the table below as $IC_{50}$ (μg/ml) and $CC_{50}$ (μg/ml), respectively. The potential therapeutic usefulness was assessed by calculating a Selectivity Index (SI) corresponding to the ratio of $CC_{50}$ to $IC_{50}$. A control test was performed using the known anti-HIV treatment AZT.

In Table 1 below, the compounds screened were:

AZT: known anti-HIV compound

A: 1,1'-[1,3-phenylenebis(methylene)]bis-1,4,8,11-tetraazacyclotetradecane

B: 1,1'-[1,4-phenylenebis(methylene)]bis-1,4,8,11-tetraazacyclotetradecane

C: 1,1'-[5-nitro-1,3-phenylenebis-(methylene)]-bis-1,4,8,11-tetraazacyclotetradecane D: 1,1'-[2,3,5,6-tetrafluoro-1,3-phenylene-bis-(methylene)]bis-1,4,8,11-tetraazacyclotetradecane E: 1,1'-[1,4-naphthylenebis(methylene)]bis-1,4,8,11-tetraazacyclotetradecane F–V: See preceding preparative Examples.

W: 1,1'-[2,5-dimethyl-1,4-phenylenebis-(methylene)]-bis-1,4,8,11-tetraazacyclotetradecane X: 1,1'-[2,5-dichloro-1,4-phenylenebis-(methylene)]-bis-1,4,8,11-tetraazacyclotetradecane Y: 1,1'-[2-bromo-1,4-phenylenebis-(methylene)]-bis-1,4,8,11-tetraazacyclotetradecane Z: 1,1'-[6-phenyl-2,4-pyridinebis-(methylene)]-bis-1,4,8,11-tetraazacyclotetradecane

TABLE 1

| | HIV-1 ($III_B$) | | | HIV-2 (ROD) | | |
|---|---|---|---|---|---|---|
| CMPD | $IC_{50}$ µg/ml | $CC_{50}$ µg/ml | SI | $IC_{50}$ µg/ml | $CC_{50}$ µg/ml | SI |
| AZT Comparison | <0.008 | >1 | >125 | — | — | — |
| A | 0.03 | >500 | $>1.5 \times 10^4$ | <0.01 | >500 | $>5 \times 10^4$ |
| B | 0.006 | >500 | $>8.3 \times 10^4$ | <0.01 | >500 | $>5 \times 10^4$ |
| C | 0.05 | 55 | 1100 | 0.07 | 55 | 756 |
| D | 0.01 | 60 | 6000 | 0.01 | 60 | 6000 |
| E | 0.07 | 71 | 1014 | 0.05 | 71 | 1420 |
| F | 0.0026 | >200 | $>7.6 \times 10^4$ | 0.0019 | >200 | $>1 \times 10^5$ |
| G | 0.018 | >200 | $>1.1 \times 10^4$ | 0.027 | >200 | $>7.4 \times 10^3$ |
| J | 0.16 | >200 | >1250 | 0.22 | >200 | >900 |
| K | 0.38 | 117 | 300 | 0.35 | 117 | 334 |
| L | 0.29 | >200 | >690 | 0.32 | >200 | >625 |
| M | 0.03 | >500 | $>1.6 \times 10^4$ | 0.07 | >500 | $>7.1 \times 10^3$ |
| N | 0.01 | >500 | $>5 \times 10^4$ | 0.07 | >500 | $>7.1 \times 10^3$ |
| O | 0.03 | >500 | $>1.6 \times 10^4$ | 0.08 | >500 | $>6.2 \times 10^3$ |
| P | 0.04 | >500 | $>1.2 \times 10^4$ | 0.09 | >500 | $>5.5 \times 10^3$ |
| Q | 0.07 | 19 | 271 | 0.5 | 19 | 38 |
| R | 0.3 | 51 | 170 | 2.2 | 51 | 23 |
| T | 0.01 | >500 | $>5.0 \times 10^4$ | 0.02 | >500 | $>2.5 \times 10^4$ |
| W | 0.0076 | >250 | $>3.2 \times 10^4$ | 0.0013 | >250 | $>1.9 \times 10^5$ |
| X | 0.0131 | 71.87 | 5461 | 0.0030 | 72.66 | $2.4 \times 10^4$ |
| Y | 0.0075 | >250 | $>3.2 \times 10^4$ | 0.0043 | >250 | $>5.7 \times 10^4$ |
| Z | 0.0489 | >250 | 5112 | 0.0246 | >250 | $1.0 \times 10^4$ |

It can readily be seen that the compounds according to the invention are highly active against HIV-1 and -2, with low toxicity, in the in vitro tests used.

The compound B, which is the most preferred compound of the invention, was further tested for antiviral effects on different laboratory strains of HIV-1 in MT-4 cells, using the MIT assay. Compound B was found to have an $IC_{50}$ in the range of 2–5 ng/ml against IIIb, RF, HE and NDK strains, showing that its high activity is remarkably strain-independent.

T4-lymphocytes and monocytes are targets for HIV-1 infection in vivo. The following test method showed that compound B inhibits virus replication also in primary T4 cells and primary monocytes in culture.

Primary T4 lymphocytes were purified from human spleens obtained from healthy donors by using a commercial kit ("Lympho-Kwik") which combines reaction of cells with specific monoclonal antibodies and density gradient centrifugation to separate the cells. Preparations obtained by this procedure contained 60–80% CD4 positive cells as analysed by FACS. Cells were stimulated with 2 µg/ml PHA for 24 hours. Then they were spun down and infected with HIV-1, strain IIIb, by suspending the cells 10-fold concentrated in virus solution. Adsorption was allowed for 2 hours at 37° C. The inoculum was removed by centrifugation and the cells were re-suspended at their original concentration in fresh culture medium containing IL-2 (40 IE/ml). Test compound was added after stimulation and virus adsorption. Every 3 to 4 days post infection half of the supernatant of the infected cultures was removed and replaced by fresh medium containing the test compound at the particular concentration, The concentration of vital p24 antigen was determined in the supernatent by means of a commercial ELISA kit (Coulter) and served as a parameter for virus production. Compound B does not interfere with the p24 Elisa test (highest concentration tested: 100 µg/ml).

Mononuclear cells were isolated from healthy, HIV-negative donors using Ficoll density separation. Cells ($4 \times 10^6$/ml) were incubated for 5 days in 48 well plates (Costar) in monocyte medium consisting of RPMII640, supplemented with 20% ECS and 10% human serum. On day 5 non-adherent cells were washed out four times with warm PBS containing 2% human serum. Preparations obtained by the procedure were >95% positive for non-specific esterase (Sigma) and cell viability (as determined by trypan blue exclusion) was always >95%.

The monocytotropic strain of HIV-1, BaL, was used for the infection of these monocyte preparations (Pemo et al, 1 Exp Meal, 169, 933, 1989).

Adherent monocytes were exposed to 50 µg/well of a 1:30 dilution of HIV-1, BaL for 30 minutes subsequently, monocyte medium was added to 1 ml/well. Adsorption was allowed for 24 hours at 37° C. Then, the wells were washed twice in order to remove excess virus and were cultivated in the presence of different drug concentrations. Thus, test compounds were added after adsorption. Every 3 to 4 days post infection the supernatant of the infected cultures was removed and replaced by fresh medium containing the test compound at the particular concentration. The concentration of viral p24 antigen was determined as described above.

$IC_{50}$ and $IC_{90}$ values were calculated by comparing the p24 antigen concentrations in supernatent of treated, infected cells and uncreated, infected cells at days 11 and 14 post infection.

Table 2 shows that Compound B is a potent inhibitor of HIV-1 replication in both primary cell types, with $IC_{90}$ values of 1–2 ng/ml. At the highest concentration tested, 100 ng/ml, no cytotoxicity was observed.

TABLE 2

Activity of Compound B and AZT against HIV-a, IIIb, replication in primary T4 lymphocytes and against HIV-1, BaL, replication in primary monocytes

| | | $IC_{50}$ (µg/ml) | | $IC_{90}$ (µg/ml) | |
|---|---|---|---|---|---|
| Compound | Cell Type | day 11 | day 14 | day 11 | day 14 |
| B | Lymphocytes | <0.001 | <0.001 | <0.001 | 0.0010 |
| AZT | Lymphocytes | 0.00045 | 0.00043 | 0.0022 | 0.0011 |
| B | Monocytes | <0.001 | 0.0011 | 0.0019 | 0.0021 |
| AZT | Monocytes | 0.0010 | 0.0010 | 0.0015 | 0.0017 |

Using the same methods, it was also shown that Compound B was a strong inhibitor of vital replication in primary T4 cells infected with low-passage primary clinical isolates of HIV-1 from three different geographical locations (K31, Zaire, D370, California, and K6/2, Germany).

The low cytotoxicity of Compound B was also shown by incubation of exponentially growing cells with Compound B or with AZT and determining cell numbers 2, 3 and 4 days after seeding. Compound B did not inhibit growth of MT4, MOLT4, HUT78, Jurkat cells (all T cell lines) nor the growth of the monocylic U937 cell line at concentrations below 300 µg/ml. With the exception of the HUT78 cells, AZT was in all cases more cytotoxic than Compound B with $TC_{50}$ values (µg/ml) of 23, 37, 184 and 5 for MT4, MOLT4, Jurkat and U937 respectively.

In contrast to HIV-protease inhibitors, the compounds of the invention do not block virus production from chronically infected cells, indicating that the antiviral target is in the early part of the infection process, before, or at, integration of the provirus. To pinpoint the stage at which the compounds interact with the HIV replicative cycle, a time-of-addition experiment was carried out on MT4 cells infected with HIV-1 strain IIIb at high virus multiplicity to ensure that the virus replicative steps would be synchronised in the whole cell populations. Test compounds wife added 1, 2, 3, . . . 22, 23, 24 hours after infection, and vital p24 antigen production determined 29 hours after infection.

Depending on the stage at which compounds interact and the need for intracellular metabolism, addition of the compounds could be delayed for n hours without loss of activity. Daxtran sulphate, which acts at the virus adsorption step, must be added together with the virus (n=0) to be active. For AZT, which, following its intercellular phosphorylation, acts at the reverse transcriptase step, addition to the cells could be delayed until ca 4 hours (n=4) after infection. For the TIBO derivative (R82913), which does not need intracellular transformation before it can interact with reverse transcriptase the addition could be delayed by another 2 hours (n=6). The protease inhibitor Ro31-8959 which interacts with a late event in the virus cycle (assembly of mature virus) was still effective if added as late as 12 hours after infection (n=12). From the time-of-addition experiment appeared that for Compound B, n=1 or 2, so that the compound must interact with a process following virus absorption but preceding reverse transcription, for example, virus-cell fusion and/or uncoating.

To obtain further evidence for the inhibitory effect of Compound B on HIV uncoating (or fusion), experiments were designed whereby the viral RNA harvested from cells that had just been infected was monitored for its sensitivity to degradation by RNase. It was reasoned that if tincoating (fusion) was hampered, the viral capsid (or envelope) proteins would remain associated with the viral RNA genome and thus the RNA should be protected against RNase attack. When MT4 cells were exposed to radiolabelled viral particles at a very high multiple of infection and then treated with different concentrations of Compound B, viral RNA harvested from the cells 4 hours after infection showed resistance to degradation by RNaseA. Vital RNA harvested from HIV-infected cells treated with other anti-HIV agents (ie AZT, DDI, R82913, or Ro31-8959) did not show this increased resistance to degradation by RNase.

In addition, Compound B was also found to inhibit fusion, which is the mechanism by which viruses enter cells and by which virus or infectious material is transmitted from cell to cell. Syncytium formation between chronically infected cells and uninfected cells reflects the gp120/41 mediated fusion process of vital entry. The syncytium inhibition assay (Baba et al, J AIDS 3 493, 1990)) using HIV-1 IIIb infected HUT78 cells with MOLT4 cells indicates that Compound B is at least as potent as dextran sulphate in inhibition of fusion. The concentrations required (approximately 1 μg/ml) are considerably higher than the antiviral $IC_{50}$ values, but are well below cytotoxicity levels.

These results strongly indicate that the compounds of the invention inhibit primarily the uncoating step and also to some extent the fusion step of the vital replicative cycle. This is a unique mode of action for anti-HIV agents, and the involvement of two distinct target steps makes it less likely that resistance to the drug will develop rapidly in treated patients.

Although no suitable animal models exist for the testing of in vivo efficacy of anti-HIV agents, testing of drug serum levels in the rabbit was carried out, and after sc administration of 10 mg/kg of Compound B, samples of rabbit serum were taken. Measurement of anti-HIV activity in the sen showed levels of the drug exceeding the in vitro $IC_{50}$ level by a factor of a hundred for at least 6 hours after administration. This indicates that the compound would have anti-HIV activity in humans or an animal susceptible to infection by HIV.

The compounds of Formula I axe therefore useful for the treatment and/or prophylaxis of HIV infection, alone or in combination with other active agents. The appropriate dosage will, of course, vary depending upon, for example, the compound of Formula I employed, the host, the mode of administration and the nature and severity of the conditions being treated. However, in general, satisfactory results in humans are indicated to be obtained at daily dosages from about 0.01–20 mg/kg of body weight. An indicated daily dosage in humans is in the range from about 0.7 mg to about 1400 mg of a compound of Formula I conveniently administered for example in divided doses up to four times a day.

The compounds of Formula I may be administered by any conventional route, particularly enterally, preferably orally, eg in the loan of tablets or capsules or in liquid form, eg as a syrup; or parenterally, eg in the form of solutions or suspensions for iv or sc administration.

Compound B is the preferred compound of Formula I. In view of its activity in the test methods as described above, it is indicated that Compound B may be administered to humans at daily dosages of from 2 to 200 mg, preferably 10 to 70 mg, by parentexal administration, eg by subcutaneous injection.

The compounds of Formula I may be administered in free base form or in pharmaceutically acceptable acid addition salt or metal complex form. Such salts and complexes may be prepaxed in conventional manner as described in the Examples, and exhibit the same order of activity as the free bases. Pharmaceutical compositions containing compounds of Formula I may be manufactured in conventional manner. Unit dosage forms contain for example from about 0.5 mg to about 100 mg of a compound of Formula I in free base or pharmaceutically acceptable acid addition salt form.

We claim:

1. A pharmaceutical composition active against HIV comprising as an active ingredient a linked cyclic compound of formula I,

Z-R-A-R'-Y (I)

in which Z and Y are identical cyclic polyamine moieties having from 10 to 15 ring members and from 3 to [6] *4* amine nitrogens in the ring spaced by 2 or more carbon atoms from each other, said amine nitrogens being the only ring heteroatoms, A is an *unsubstituted* aromatic or heteroaromatic moiety other than quinoline, R and R' are each methylene linked to nitrogen atoms in Z and Y, the amine nitrogen atoms being otherwise unsubstituted, *in admixture or association with a pharmaceutically acceptable diluent or carrier*.

2. A composition according to claim 1, wherein in the compound of formula I, each moiety Z and Y has 14 ring members and 4 amine nitrogens in the ring.

3. A *pharmaceutical* composition [according to claim 1, wherein the] *active against HIV comprising as an* active ingredient [is] 1,1'-[1,3-phenylenebis(methylene)]-bis-1,4,8,11-tetra-azacyclotetradecane in acid addition salt form *in admixture or association with a pharmaceutically acceptable diluent or carrier*.

4. A *pharmaceutical* composition [according to claim 1, wherein the] *active against HIV comprising as an* active ingredient [is] 1,1'-[1,4-phenylenebis(methylene)]-bis-1,4,8,11-tetra-azacyclotetradecane in acid addition salt form *in admixture or association with a pharmaceutically acceptable diluent or carrier.*

5. A *pharmaceutical* composition [according to claim 1, wherein the] *active against HIV comprising as an* active ingredient [is] a bis-zinc complex of 1,1'-[1,4-phenylene-bis-(methylene)]-bis-1,4,8,11-tetraazacyclotetradecane *in admixture or association with a pharmaceutically acceptable diluent or carrier.*

6. A *pharmaceutical* composition [according to claim 1, wherein the] *active against HIV comprising as an* active ingredient [is] a bis-copper complex of 1,1'-[1,4-phenylene-bis-(methylene)]-bis-1,4,8,11-tetraazacyclotetradecane *in admixture or association with a pharmaceutically acceptable diluent or carrier.*

7. A *pharmaceutical* composition [according to claim 1, wherein the] *active against HIV comprising as an* active ingredient [is] 1,1'-[3,3'-biphenylene-bis-(methylene)]-bis-1,4,8,11-tetraazacyclotetradecane in acid addition salt form *in admixture or association with a pharmaceutically acceptable diluent or carrier.*

8. A *pharmaceutical* composition [according to claim 1, wherein the] *active against HIV comprising as an* active ingredient [is 11,11'-[1,4-phenylene-bis-(methylene)]-bis-1,4,7,11-tetraazacyclotetradecane] *11,11'-[1,4-phenylene-bis-(methylene)]-bis-1,4,7,11-tetraazacyclotetradecane* in acid addition salt form *in admixture or association with a pharmaceutically acceptable diluent or carrier.*

9. A *pharmaceutical* composition [according to claim 1, wherein the] *active against HIV comprising as an* active ingredient [is] 1,11'-[1,4-phenylene-bis-(methylene)]-1,4,8,11-tetraazacyclotetradecane-1,4,7,11-tetraazacyclotetradecane in acid addition salt form *in admixture or association with a pharmaceutically acceptable diluent or carrier.*

10. A *pharmaceutical* composition [according to claim 1, wherein the] *active against HIV comprising as an* active ingredient [is] 1,1'-[2,6-pyridine-bis-(methylene)]-bis-1,4,8,11-tetraazacyclotetradecane in acid addition salt form *in admixture or association with a pharmaceutically acceptable diluent or carrier.*

11. A *pharmaceutical* composition [according to claim 1, wherein the] *active against HIV comprising as an* active ingredient [is] 1,1-[3,5-pyridine-bis-(methylene)]-bis-1,4,8,11-tetraazacyclotetradecane in acid addition salt form *in admixture or association with a pharmaceutically acceptable diluent or carrier.*

12. A *pharmaceutical* composition [according to claim 1, wherein the] *active against HIV comprising as an* active ingredient [is] 1,1'-[2,5-thiophene-bis-(methylene)]-bis-1,4,8,11-tetraazacyclotetradecane in acid addition salt form *in admixture or association with a pharmaceutically acceptable diluent or carrier.*

13. A *pharmaceutical* composition [according to claim 1, wherein the] *active against HIV comprising as an* active ingredient [is] 1,1'-[4,4'-(2,2'-bipyridine)-bis-(methylene)]-bis-1,4,8,11-tetraazacyclotetradecane in acid addition salt form *in admixture or association with a pharmaceutically acceptable diluent or carrier.*

14. A *pharmaceutical* composition [according to claim 1, wherein the] *active against HIV comprising as an* active ingredient [is] 1,1'-[2,9-(1,10-phenanthroline)-bis-(methylene)]-bis-1,4,8,11-tetraazacyclotetradecane in acid addition salt form *in admixture or association with a pharmaceutically acceptable diluent or carrier.*

15. A *pharmaceutical* composition [according to claim 1, wherein the] *active against HIV comprising as an* active ingredient [is] 1,1'-[1,3-phenylene-bis-(methylene)]-bis-1,4,7,10-tetraazacyclotetradecane in acid addition salt form *in admixture or association with a pharmaceutically acceptable diluent or carrier.*

16. A *pharmaceutical* composition [according to claim 1, wherein the] *active against HIV comprising as an* active ingredient [is] 1,1'-[1,4-phenylene-bis-(methylene)]-bis-1,4,7,10-tetraazacyclotetradecane in acid addition salt form *in admixture or association with a pharmaceutically acceptable diluent or carrier.*

17. [The compound of claim 1, which is] *A pharmaceutical composition active against HIV comprising as an active ingredient* 1,1'-[5-nitro-1,3-phenylenebis(methylene)]bis-1,4,8,11-tetraazacyclotetradecane in acid addition salt form *in admixture or association with a pharmaceutically acceptable diluent or carrier.*

18. [The compound of claim 1, which is 1'1'-[2,4,5,6-tetrachloro-1,3-phenyleneis(methylene)]bis-1,4,8,11-tetraazacyclotetradecane] *A pharmaceutical composition active against HIV comprising as an active ingredient 1'1'-[2,4,5,6-tetrachloro-1,3-phenylenebis(methylene)]bis-1,4,8,11-tetraazacyclotetradecane* in acid addition salt form *in admixture or association with a pharmaceutically acceptable diluent or carrier.*

19. [The compound of claim 1, which is] *A pharmaceutical composition active against HIV comprising as an active ingredient* 1,1'-[2,3,5,6-tetrafluoro-1,4-phenylenebis(methylene)]bis-1,4,8,11-tetraazacyclotetradecane in acid addition salt form *in admixture or association with a pharmaceutically acceptable diluent or carrier.*

20. [The compound of claim 1, which is] *A pharmaceutical composition active against HIV comprising as an active ingredient* 1,1'-[1,4-naphthylene-bis-(methylene)]bis-1,4,8,11-tetraazacyclotetradecane in acid addition salt form *in admixture or association with a pharmaceutically acceptable diluent or carrier.*

21. [The compound of claim 1, which is] *A pharmaceutical composition active against HIV comprising as an active ingredient* 1,1'-[1,3-phenylenebis-(methylene)]bis-1,5,9-triazacyclododecane in acid addition salt form *in admixture or association with a pharmaceutically acceptable diluent or carrier.*

22. [The compound of claim 1, which is 1,1'-[1,4-phenylene-bis-(methylene)]-1,5,9-triazacyclododecane] *A pharmaceutical composition active against HIV comprising as an active ingredient 1,1'-[1,4-phenylene-bis-(methylene)]-bis-1,5,9-triazacyclododecane* in acid addition salt form *in admixture or association with a pharmaceutically acceptable diluent or carrier.*

[23. The compound of claim 1, which is a bis-zinc complex of 1,1'[1,4-phenylene-bis-(methylene)]-bis-1,4,8,11-tetraazacyclotetradecane.]

[24. The compound of claim 1, which is 1,1'-[3,3'-biphenylene-bis-(methylene)]-bis-1,4,8,11-tetraazacyclotetradecane in acid addition salt form.]

[25. The compound of claim 1, which is 1,1'-[2,6-pyridine-bis-(methylene)]-bis-1,4,8,11-tetraazacyclotetradecane in acid addition salt form.]

[26. The compound of claim 1, which is 1,1'-[3,5-pyridine-bis-(methylene)]-bis-1,4,8,11-tetraazacyclotetradecane in acid addition salt form.]

[27. The compound of claim 1, which is 1,1'-[2,5-thiophene-bis-(methylene)]-bis-1,4,8,11-tetraazacyclotetradecane in acid addition salt form.]

[28. The compound of claim 1, which is 1,1'-[4,4'-(2,2'-bipyridine)-bis-(methylene)]-bis-1,4,8,11-tetraazacyclotetradecane in acid addition salt form.]

[29. The compound of claim 1, which is 1,1'-[2,9-(1,10-phenanthroline)-bis-(methylene)]-bis-1,4,8,11-tetraazacyclotetradecane in acid addition salt form.]

[30. The compound of claim 1, which is 1,1'-[1,3-phenylene-bis-(methylene)]-bis-1,4,7,10-tetraazacyclotetradecane in acid addition salt form.]

[31. The compound of claim 1, which is 1,1'-[1,4-phenylene-bis-(methylene)]-bis-1,4,7,10-tetraazacyclotetradecane in acid addition salt form.]

32. [The compound of claim 1, which is] *A pharmaceutical composition active against HIV comprising as an active ingredient* 1,1'-[2,5-dimethyl-1,4-phenylenebis-(methylene)]-bis-1,4,8,11-tetraazacyclotetradecane *in admixture or association with a pharmaceutically acceptable diluent or carrier.*

33. [The compound of claim 1, which is] *A pharmaceutical composition active against HIV comprising as an active ingredient* 1,1'-[2,5-dichloro-1,4-phenylenebis-(methylene)]-bis-1,4,8,11-tetraazacyclotetradecane *in admixture or association with a pharmaceutically acceptable diluent or carrier.*

34. [The compound of claim 1, which is] *A pharmaceutical composition active against HIV comprising as an active ingredient* 1,1'-[2-bromo-1,4-phenylenebis-(methylene)]-bis-1,4,8,11-tetraazacyclotetradecane *in admixture or association with a pharmaceutically acceptable diluent or carrier.*

35. [The compound of claim 1, which is] *A pharmaceutical composition active against HIV comprising as an active ingredient* 1,1'-[6-phenyl-2,4-pyridinebis-(methylene)]-bis-1,4,8,11-tetraazacyclotetradecane *in admixture or association with a pharmaceutically acceptable diluent or carrier.*

*36. A pharmaceutical composition active against HIV comprising as an active ingredient 1,1'-[1,3-phenylenebis (methylene)]-bis-1,4,8,11-tetra-azacyclotetradecane in admixture or association with a pharmaceutically acceptable diluent or carrier.*

*37. A pharmaceutical composition active against HIV comprising as an active ingredient 1,1'-[1,4-phenylenebis (methylene)]-bis-1,4,8,11-tetra-azacyclotetradecane in admixture or association with a pharmaceutically acceptable diluent or carrier.*

*38. A pharmaceutical composition active against HIV comprising as an active ingredient 1,1'-[3,3'-biphenylene-bis-(methylene)]-bis-1,4,8,11-tetraazacyclotetradecane in admixture or association with a pharmaceutically acceptable diluent or carrier.*

*39. A pharmaceutical composition active against HIV comprising as an active ingredient 11,11'-[1,4-phenylene-bis-(methylene)]-bis-1,4,7,11-tetraazacyclotetradecane in admixture or association with a pharmaceutically acceptable diluent or carrier.*

*40. A pharmaceutical composition active against HIV comprising as an active ingredient 1,1'-[2,6-pyridine-bis-(methylene)]-bis-1,4,8,11-tetraazacyclotetradecane in admixture or association with a pharmaceutically acceptable diluent or carrier.*

*41. A pharmaceutical composition active against HIV comprising as an active ingredient 1,1-[3,5-pyridine-bis-(methylene)]-bis-1,4,8,11-tetraazacyclotetradecane in admixture or association with a pharmaceutically acceptable diluent or carrier.*

*42. A pharmaceutical composition active against HIV comprising as an active ingredient 1,1'-[2,5-thiophene-bis-(methylene)]-bis-1,4,8,11-tetraazacyclotetradecane in admixture or association with a pharmaceutically acceptable diluent or carrier.*

*43. A pharmaceutical composition active against HIV comprising as an active ingredient 1,1'-[4,4'-(2,2'-bipyridine)-bis-(methylene)]-bis-1,4,8,11-tetraazacyclotetradecane in admixture or association with a pharmaceutically acceptable diluent or carrier.*

*44. A pharmaceutical composition active against HIV comprising as an active ingredient 1,1'-[2,9-(1,10-phenanthroline)-bis-(methylene)]-bis-1,4,8,11-tetraazacyclotetradecane in admixture or association with a pharmaceutically acceptable diluent or carrier.*

*45. A pharmaceutical composition active against HIV comprising as an active ingredient 1,1'-[1,3-phenylene-bis-(methylene)]-bis-1,4,7,10-tetraazacyclotetradecane in admixture or association with a pharmaceutically acceptable diluent or carrier.*

*46. A pharmaceutical composition active against HIV comprising as an active ingredient 1,1'-[1,4-phenylene-bis-(methylene)]-bis-1,4,7,10-tetraazacyclotetradecane in admixture or association with a pharmaceutically acceptable diluent or carrier.*

*47. A pharmaceutical composition active against HIV comprising as an active ingredient 1,1'-[5-nitro-1,3-phenylenebis(methylene)]bis-1,4,8,11-tetraazacyclotetradecane in admixture or association with a pharmaceutically acceptable diluent or carrier.*

*48. A pharmaceutical composition active against HIV comprising as an active ingredient 1'1'-[2,4,5,6-tetrachloro-1,3-phenylenebis(methylene)]bis-1,4,8,11-tetraazacyclotetradecane in admixture or association with a pharmaceutically acceptable diluent or carrier.*

*49. A pharmaceutical composition active against HIV comprising as an active ingredient 1,1'-[2,3,5,6-tetra-fluoro-1,4-phenylenebis(methylene)]bis-1,4,8,11-tetraazacyclotetradecane in admixture or association with a pharmaceutically acceptable diluent or carrier.*

*50. A pharmaceutical composition active against HIV comprising as an active ingredient 1,1'-[1,4-naphthylene-bis-(methylene)]bis-1,4,8,11-tetraazacyclotetradecane in admixture or association with a pharmaceutically acceptable diluent or carrier.*

*51. A pharmaceutical composition active against HIV comprising as an active ingredient 1,1'-[1,3-phenylenebis-(methylene)]bis-1,5,9-triazacyclododecane in admixture or association with a pharmaceutically acceptable diluent or carrier.*

*52. A pharmaceutical composition active against HIV comprising as an active ingredient 1,1'-[1,4-phenylene-bis-(methylene)]-bis-1,5,9-triazacyclododecane in admixture or association with a pharmaceutically acceptable diluent or carrier.*

* * * * *